United States Patent
Li et al.

(10) Patent No.: US 9,366,607 B2
(45) Date of Patent: Jun. 14, 2016

(54) SAMPLE LINE MANAGEMENT IN A FLUID ANALYZER SYSTEM

(71) Applicant: Thermo Environmental Instruments Inc., Franklin, MA (US)

(72) Inventors: Yonquan Li, Schenectady, NY (US); Daniel E. Glenn, Westwood, MA (US); K. Stephen Johnson, Jr., Plymouth, MA (US); Dieter Kita, Blackstone, MA (US)

(73) Assignee: Thermo Environmental Instruments Inc., Franklin, MA (US)

( * ) Notice: Subject to any disclaimer, the term of this patent is extended or adjusted under 35 U.S.C. 154(b) by 526 days.

(21) Appl. No.: 13/714,618

(22) Filed: Dec. 14, 2012

(65) Prior Publication Data

US 2014/0165705 A1 Jun. 19, 2014

(51) Int. Cl.
*G01N 1/44* (2006.01)
*G01N 33/00* (2006.01)
*G01N 1/22* (2006.01)

(52) U.S. Cl.
CPC .............. *G01N 1/44* (2013.01); *G01N 33/0009* (2013.01); *G01N 1/2247* (2013.01)

(58) Field of Classification Search
None
See application file for complete search history.

(56) References Cited

U.S. PATENT DOCUMENTS

| | | | |
|---|---|---|---|
| 3,334,513 A | 8/1967 | Thomas | |
| 5,089,134 A | 2/1992 | Ando et al. | |
| 5,114,447 A | 5/1992 | Davis | |
| 6,136,281 A | 10/2000 | Meischen et al. | |
| 7,517,511 B2 | 4/2009 | Schofield | |
| 2006/0159605 A1 | 7/2006 | Seames et al. | |
| 2006/0246594 A1* | 11/2006 | Appel | G01N 21/6408 436/81 |
| 2008/0202207 A1* | 8/2008 | Moore | G01N 33/0045 73/23.31 |
| 2008/0282764 A1 | 11/2008 | Holt et al. | |

* cited by examiner

*Primary Examiner* — Robert R Raevis
(74) *Attorney, Agent, or Firm* — William R. McCarthy, III

(57) ABSTRACT

In a first mode, a monitoring system inputs humidified gas through at least a portion of a conduit. At least a portion of the water in the humidified gas adheres to the inner surface of the conduit, inhibiting contaminants in the gas sample from adhering to the inner surface. The water in the humidified gas may also push any contaminants adhered to the surface of the sample line back out the sample line. In a second mode, after previously passing the humidified gas through the conduit, the monitoring system controls a flow of a gas sample including the contaminants through the conduit to a gas analyzer. The one or more layer of water on the inner surface of the conduit prevents or reduces a buildup of undesirable contaminants on an inner surface of a conduit that conveys gas samples.

23 Claims, 8 Drawing Sheets

SAMPLE LINE MANAGEMENT IN A FLUID ANALYZER SYSTEM

BACKGROUND

Conventional emission sources sometimes emit undesirable substances such as Ammonia (e.g., $NH_3$), Hydrogen Chloride (e.g., HCl), Ammonium Chloride (e.g., $NH_4Cl$), etc. The emission of these and other manufacturing byproducts at high concentrations into the atmosphere is often undesirable. Accordingly, it is a common requirement to have to continuously monitor a respective smoke stack for pollution to control emissions of certain types of pollution to be below threshold concentration levels.

Typically, continuous monitoring of an emission resource requires that a gas sample received from emission resource be conveyed to a monitoring system a short distance away. Conventional monitoring systems have the ability to monitor a concentration of different undesirable pollutants in the received gas sample.

It is often challenging to convey substances such as HCl, $NH_3$, etc., in a sample line from a stack to a respective monitoring system because such substances tend to be sticky. That is, these particular pollutants readily stick to an inner surface of a conduit that conveys the respective gas sample from the stack to the monitoring system. In addition to being sticky, these substances are chemically reactive and can easily convert into undesirable byproducts such as ammonium chloride particles ($NH_4Cl$), which also readily stick to inner walls of the sample line.

One outstanding issue with conventional monitoring systems is the positive zero offset caused by condensation of HCl and $NH_3$ on inner walls of the conduit and the dissociation of $NH_4Cl$ particles after a long-term operation of the monitoring system. In other words, walls of a conduit conveying a respective gas sample from a source (such as a stack) to the monitoring system eventually can be contaminated or clogged with pollutants, impairing an ability of the monitoring system to accurately perform the function of monitoring pollutants.

In certain instances, such as when the sample line becomes clogged or lined with pollutants, the monitoring system may need to be shut down so that a technician can manually clean the sample line. In a worst scenario, when a conveyance line is so clogged, the technician will need to replace filters, probes, sample lines, etc., to restore a monitoring back to normal operation. As may be expected, physical replacement can be costly because a manufacturing plant may need to be shut down during replacement of components. The facility shut down can also cause the significant down time of emission monitoring system. As a result, the high payment for meeting emission compliance would be anticipated.

BRIEF DESCRIPTION OF EMBODIMENTS

Certain conventional monitoring systems attempt to address issues of contaminants sticking to inner walls of a sample line via a process known as blowback. As its name suggests, conventional blowback involves transmitting short bursts of air in a reverse direction through a respective filter to prevent the respective filter from becoming clogged. Unfortunately, field tests have shown that conventional blowback is ineffective to prevent filters from clogging. In fact, in many instances, conventional blowback techniques appears to make matters worse as it tends to quickly cool down a respective sample line and filter, resulting in subsequent condensation or the reformation of pollutants such as $NH_4Cl$ on inner walls of the conduit.

In contrast to conventional techniques, in general, embodiments herein include novel techniques of reducing an amount of contaminants that adhere to inner walls of a sample line.

More specifically, according to one embodiment, a monitoring system receives a first mode control signal to operate in a first mode. In accordance with the first mode control signal, the monitoring system inputs humidified gas through at least a portion of a conduit (such as a sample line) to inhibit contaminants from adhering to an inner surface of the conduit. The monitoring system then receives a second mode control signal indicating to operate in a second mode. In accordance with the second mode control signal, after previously passing the humidified gas through the conduit, the monitoring system controls a flow of a gas sample including the contaminants through the conduit to a gas analyzer. At least a portion of the water in the humidified gas in the first mode adheres to the inner surface of the conduit, inhibiting the contaminants in the gas sample from adhering to the inner surface. Via this technique, embodiments herein include preventing a buildup of undesirable contaminants on an inner surface of a conduit that conveys gas samples.

In more specific embodiments, in accordance with the second mode control signal and while in the second mode, the monitoring system controls a flow of a gas sample in a forward direction from a sample gas source such as a smokestack through a conduit to a gas analyzer. Further in the second mode, in one embodiment, the gas analyzer samples presence of contaminants in the gas sample. Assume the monitoring system then receives a first mode control signal again to operate in the first mode. In accordance with the first mode control signal and while in the first mode, the monitoring system inputs humidified gas in a reverse direction through at least a portion of the conduit to the sample gas source. As previously discussed, inputting and passing the humidified gas through the conduit causes one or more layers of water to be adsorbed onto the inner surface of the conduit. All or a portion of the original one or more layers of water adsorbed onto the inner surface may have been removed during the second mode when the gas sample passes through the conduit. In one embodiment, the humidified gas passes though at least a portion of the conduit in a first direction; the sample gas passes through the conduit in a second direction being substantially opposite the first direction.

In one embodiment, the sample will contain more water than an amount of water in the flowback mode, but the water in the sample may be contaminated with Hydrochloric Acid and Ammonium Chloride where the flowback mode contains clean water to wash out the sample line. Prior art techniques would just leave the sample line stagnant or run dry zero air back through the line, causing it to dry out.

In one embodiment, inputting the humidified gas in the reverse direction through at least a portion of the conduit prevents or reduces a likelihood that water soluble substances such as Ammonia (e.g., $NH_3$), Hydrochloric Acid (e.g., HCl), Ammonium Chloride (e.g., $NH_4Cl$), Ammonium Nitrate (e.g., $NH_4NO_3$), Sulfate (e.g., $(NH_4)_2SO_4$), etc., in the sample gas will subsequently adhering to the inner surface of the conduit when sampling again. In addition to preventing at least a portion of the contaminants in the gas sample from sticking to the inner surface of the conduit, the passing of the humidified gas through the conduit can serve to remove or facilitate removal of contaminants from adhering to the inner surface of the conduit.

Thus, after operating in the first mode (such as a flow back mode) to potentially remove pollutants off the inner wall of the conduit and/or adsorb water onto the inner wall of the conduit, the monitoring system operates in the second mode again during which the gas sample from the source is conveyed again in a forward direction on the conduit to the gas analyzer.

As mentioned, the water adsorbed onto the inner surface or walls of the conduit prevents pollutants such as Ammonia (e.g., $NH_3$), Hydrochloric Acid (e.g., HCl), Ammonium Chloride (e.g., $NH_4Cl$), Ammonium Nitrate (e.g., $NH_4NO_3$), Sulfate (e.g., $(NH_4)_2SO_4$), etc., in the gas sample from sticking to the inner surface. Accordingly, embodiments herein include exposing the inner surface of the conduit to the humidified gas including water to reduce clogging of the conduit by contaminants present in the conveyed gas sample, such as water soluble contaminants (for example, any of those previously listed).

In accordance with yet another embodiment, even though the inner surface or walls of the conduit may be coated with water or other suitable substance during an initial flow back mode, assuming that the gas sample from the source includes contaminants, at least a portion of contaminants in the gas sample may adhere to an inner surface of the conduit. Subsequently operating the monitoring system in a flow back adheres a new layer of water onto the inner surface of the conduit. As mentioned, the humidified gas may also have the affect of removing contaminants from the inner surface of the conduit. In accordance with one embodiment, repeatedly toggling between the first mode and second mode reduces buildup of contaminants in the gas sample on an inner surface of the conduit.

In yet another embodiment, the flow of a gas (e.g., a gas sample or humidified gas) in a forward and/or reverse direction through the conduit is substantially constant to prevent adsorption of contaminants onto the inner surface of the conduit. In other words, one embodiment includes ensuring that a gas always flows though the conduit either in a forward and/or reverse direction. Because a gas is substantially always moving through conduit, it is less likely that contaminants will adhere to the inner surface of the conduit. By way of a non-limiting example, a time between toggling between the first mode and second mode can be very small or even zero to provide substantially continuous flow of gas.

The conduit (e.g., sample line, tube, hose, etc.) as discussed herein can be made from any suitable material. By way of a non-limiting example, the conduit itself or at least the inner surface or inner walls of the conduit can be configured to include or be made of fluorocarbon-based material such as Polytetrafluoroethylene (PTFE) or Perfluoroalkoxy (PFA). The fluorocarbon-based material at least on the inner surface of the conduit reduces a likelihood that a contaminant in the gas sample will adhere to the inner surface of the conduit.

The dimensions of the conduit can vary depending on the application. By way of a non-limiting example, the inner diameter of the conduit is approximately 0.125 inches; the outer diameter of the conduit can be 0.25 inches. In many embodiments, an inner diameter of the conduit would fall in a range between 0.01 and 10.0 inches. The conduit can be any suitable length such as between less than an inch and more than 50 feet long depending on an application.

As previously discussed, one embodiment herein includes adsorbing one or more layers of water onto the inner surface of the conduit. To support adsorption, as opposed to condensation, the concentration of water in the humidified gas can be maintained at an appropriate level such that the water in the humidified gas does not condense onto the inner surface of the conduit. In other words, the concentration of water can be controlled such that the relative humidity of the humidified gas passing through the conduit is substantially below a relative humidity of 100%.

In certain instances, condensation of water or an excess amount of water on the inner surface may be undesirable because the subsequent release of water molecules on the inner surface into the gas sample (during a sampling mode) can interfere with subsequent testing of contaminants in the gas sample by the gas analyzer. That is, if water condenses (i.e., converts to liquid water) on the inner surface when passing the humidified gas through the gas sample, subsequent evaporation of the water off of the inner surface during the sampling mode may impede the ability of the gas analyzer to determine an actual concentration of substances present in the gas sample.

In accordance with further embodiments, note that the conduit can be heated to a temperature above a boiling point of the gas sample such as more than 100 degrees Celsius. By way of a non-limiting example, the temperature of the conduit can be set to 185 degrees Celsius. A controller in the monitoring system can control the humidified gas to include a concentration of water between 0.1% and 40.0%. By way of a non-limiting example, the relative humidity of the humidified gas as it passes through the conduit may fall between a range between 25% and 99%.

As previously discussed, further embodiments herein can include switching between the first mode and second mode depending on settings of one or more monitored parameters. In one example embodiment, in response to detecting that a concentration of contaminants in the gas sample is above a threshold value, the monitoring system can be controlled to toggle between operating in the first mode and operating in the second mode to reduce buildup of contaminants in the gas sample on an inner surface of the conduit. If the concentration of contaminants is below a threshold value, the monitoring system need not operate in the toggle mode. However, at least occasionally, it may be desirable to operate in the flow back mode (i.e., first mode) to clean the inner surface of the conduit and/or adhere one or more layers of water to the inner surface.

The trigger condition to switch from a sampling mode to a toggle mode can be based at least in part on time. For example, in response to detecting that a concentration of contaminants in the gas sample is above a threshold concentration value for more than a threshold amount of time, the monitoring system can be configured to repeat cycles of switching between operating in the first mode followed by operating in the second mode to reduce buildup of contaminants in the gas sample on an inner surface of the conduit.

Note that the humidified and/or heated gas can be generated in any suitable manner. For example, in one embodiment, the monitoring system receives zero air (e.g., ambient air in a vicinity of the monitoring system). The received gas (e.g., air) can be filtered. By way of a non-limiting example, to generate the humidified gas, the monitoring system bubbles the zero air through or passes the zero air over a water reservoir. The water reservoir can include any suitable type of water such as de-ionized water, distilled water, purified water, etc., to produce the humidified gas.

Exposing the received gas such as zero air to the water increases a concentration of the amount of water in the humidified gas to a desired level for adsorption of the one or more layers of water onto the inner surface. As previously discussed, the concentration of the water in the humidified gas can be controlled to prevent condensation of water onto the inner surface of the conduit.

The contaminants HCl, $NH_3$, $NH_4Cl$, $NH_4NO_3$, $(NH_4)_2SO_4$ etc., are all water soluble. As mentioned, the flow back of hot and/or humidified (wet) zero air into the sampling system facilitates removal of these compounds from wall surfaces of the conduit. In one embodiment, since the sampling system is heated to be above 185 degrees Celsius, or the humidified gas is pre-heated, the humidified gas is hot and wet, speeding up removal of the soluble HCl, $NH_3$, $NH_4Cl$, $NH_4NO_3$, $(NH_4)_2SO_4$ etc., on the inner surface of the conduit.

These and other more specific embodiments are disclosed in more detail below.

Note that embodiments herein can include a configuration of one or more computerized devices, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations (e.g., mode control) as summarized above and disclosed in detail below. One such embodiment comprises a computer program product including a non-transitory computer-readable storage medium (i.e., any computer readable hardware storage medium) on which software instructions are encoded for subsequent execution. The instructions, when executed in a computerized device having a processor, program and/or cause the processor to perform the operations disclosed herein. Such arrangements are typically provided as software, code, instructions, and/or other data (e.g., data structures) arranged or encoded on a non-transitory (i.e., non carrier wave) computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

For example, one embodiment includes a computer readable storage medium or computer readable hardware medium having instructions stored thereon. The instructions, when executed by a processor of a respective computer device, cause the processor or multiple processors to: receive a first mode control signal indicating to operate in a first mode; in accordance with the first mode control signal, input humidified gas through at least a portion of a conduit to inhibit contaminants from adhering to an inner surface of the conduit through which a gas sample subsequently passes; receive a second mode control signal indicating to operate in a second mode; and in accordance with the second mode control signal, control a flow of the gas sample including the contaminants from a source through the conduit to a gas analyzer.

The ordering of the steps above has been added for clarity sake. These steps can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or a within a software application.

As discussed, techniques herein are well suited for use in applications such as gas or fluid sample systems. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations, elements, aspects, etc.) of the invention(s), the reader is directed to the textual Detailed Description section and corresponding figures of the present disclosure as further discussed below. The following Detailed Description, in addition to providing an intricate description of details of the invention, also provides a further summary of aspects of the invention or inventions.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION

By way of a non-limiting example, in one embodiment, a monitoring system includes a conduit (e.g., sample line, tube, pipe, duct channel, etc.) to convey a gas sample from a sample gas source such as a stack to a gas analyzer. In a first mode, the monitoring system inputs humidified gas through at least a portion of a conduit. At least a portion of the water in the humidified gas adheres to the inner surface (e.g., walls, lining, inner coating, etc.) of the conduit. The water adhering to the inner surface of the conduit inhibits contaminants in the gas sample from sticking to the conduit. Passing of the humidified gas through the conduit may also remove contaminants from the inner walls of the conduit. In a second mode, after previously passing the humidified gas through the conduit, the monitoring system controls a flow of the gas sample including the contaminants through the conduit to a gas analyzer. The one or more layer of water on the inner surface of the conduit prevents or reduces an amount of buildup of undesirable contaminants on an inner surface of a conduit that conveys gas samples.

Figure 1:
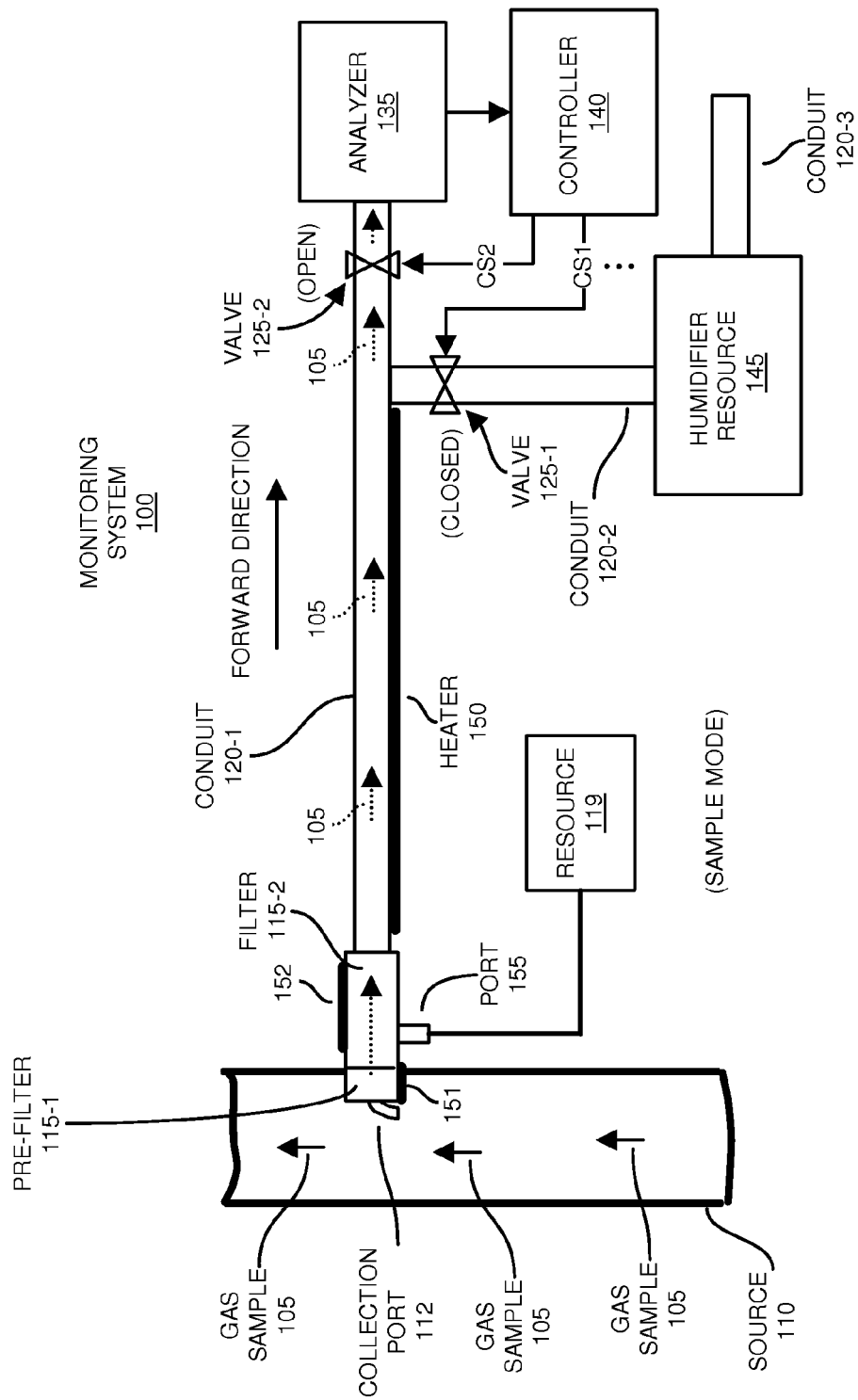
FIG. 1 is an example diagram illustrating a monitoring system operating in a sampling mode according to embodiments herein.

FIG. 1 is an example diagram illustrating a monitoring system operating in a sampling mode according to embodiments herein.

As shown, monitoring system 100 includes a source 110 such as a stack through which gas sample 105 flows. In one embodiment, gas sample 105 represents a hot, wet stack gas received from source 110. Collection port 112 receives at least a portion of the gas sample 105 passing though source 110 and redirects it through pre-filter 115-1 and filter 115-2 to conduit 120-1. Certain embodiments need not include a pre-filter 115-1.

In one embodiment, when in a sample mode, a combination of the pre-filter 115-1, filter 115-2, and the conduit 120-1 conveys gas sample 105 to analyzer 135 for detection of one or more contaminants therein.

By way of a non-limiting example, pre-filter 115-1 can be configured to remove first sized particles (or particles within a first range) from received gas sample 105. Heater 151 heats pre-filter 115-2 to 250 degrees Celsius. Filter 115-2 removes second sized particles (or particles within a first range) from received gas sample 105. Heater 152 heats pre-filter 115-2 to 200 degrees Celsius. By way of a non-limiting example, filter 115-2 can be made of ceramic or stainless steel and coated with a Silicon Dioxide material.

Conduit 120-1 receives the gas sample 105 from filter 115-2. In one embodiment, heater 150 heats conduit 120-1 to a temperature of 185 degrees Celsius.

In one embodiment, the temperature of resources such as the pre-filter 115-1, filter 115-2, and conduit 120-1 are controlled to sufficiently high values to prevent condensation of possible contaminants (such as Ammonia (e.g., NH3), Hydrochloric Acid (e.g., HCl), Ammonium Chloride (e.g., NH4Cl), Ammonium Nitrate (e.g., NH4NO3), Ammonium Sulfate (e.g., (NH4)2SO4), etc.,) on respective inside walls of the conduit 120-1 and filters 115. In other words, each of heaters 151, 152, 150 can be set to heat the gas sample to a temperature (not necessarily the specific values as indicated above) substantially above a dew point of each contaminant in the gas sample 105.

The heaters 151, 152, and 150 can produce a temperature gradient. For example, heater 151 can be configured to heat pre-filter 115-1 to a substantially higher temperature than a temperature of filter 115-2; heater 152 can be configured to heat filter 115-2 to a substantially higher temperature than a temperature of conduit 120-1.

The conduit 120-1 and filters 115 (i.e., pre-filter 115-1 and filter 115-2) as discussed herein can be made from any suitable material.

By further way of a non-limiting example, all or a portion of the conduit 120-1 can be made of fluorocarbon-based material such as Polytetrafluoroethylene (PTFE) or Perfluoroalkoxy PFA. The fluorocarbon-based material (or other suitable material) at least on the inner surface of the conduit 120-1 reduces a likelihood that one or more respective contaminants present in the gas sample 105 will adhere to the inner surface of the conduit 120-1 in the sampling mode.

The dimensions of the conduit 120-1 can vary depending on the application. In one embodiment, the inner diameter of the conduit 120-1 (through which the gas sample 105 and humidified gas 205-B pass during different modes) is approximately 0.125 inches; the outer diameter of the conduit can be 0.25 inches.

In many different possible embodiments of monitoring system 100, an inner diameter of the conduit 120-1 would fall in a range between 0.01 and 10.0 inches. The conduit 120-1 can be of any suitable length such as between less than an inch and more than 50 feet long. A length of the conduit 120-1 depends on how close the analyzer 135 can be disposed with respect to the source 110 from which the gas sample 105 is received and monitored.

By way of a non-limiting example, the flow gas sample 105 though the conduit 120-1 to the analyzer 135 can fall within a range between one and twenty liters per minute, although this flow rate may fall outside of this range depending on the embodiment.

In accordance with further embodiments, note that the humidifier resource 145 can be configured to control the humidified gas to include a concentration of water within a range between 0.1% and 95%. In certain instances, a higher water concentration in the humidified gas is desirable to remove contaminants from sample line inner surfaces. It may be possible to increase this upper limit to 95% or higher (such as up to 99%) since the water would not condense if the sample line temperature is above 100 Celsius.

Controller 140 produces at least control signals CS1 and CS2 (e.g., mode control signals) to control respective valve 125-1 and valve 125-2. While in a sampling mode, via generation of control signal CS2, the controller 140 controls the valve 125-2 at an end of the conduit 120-1 opposite the source 110 to be in an OPEN position. The open position of the valve 125-2 causes and/or enables a flow of the gas sample 105 from the source 110 through conduit 120-1 to the analyzer 135. In one embodiment, the analyzer 135 is a gas analyzer.

Note additionally that while in the sampling mode, via control signal CS1, the controller 140 controls valve 125-1 disposed between humidifier resource 145 and the conduit 120-1 to a closed position to prevent humidified gas produced by the humidifier resource 145 from being inputted into the conduit 120-1 and interfering with sampling.

As previously discussed, in the sampling mode, as its name suggests, analyzer 135 analyzes the gas sample 105 received from conduit 120-1. By way of a non-limiting example, the analyzer 135 uses Fourier Transform Infrared Spectroscopy (FTIR) techniques to detect a concentration of one or more contaminants in the gas sample 105. However, note that analyzer 135 can be any suitable type of resource capable of determining a concentration of contaminants present in the gas sample 105.

As previously discussed, certain conventional monitoring systems attempt to address issues of contaminants sticking to inner walls of a sample line via a process known as blowback. Conventional blowback involves applying short bursts of relatively high pressure air in a reverse direction down a sample line to prevent a respective filter and sample line from becoming clogged by loose particles in the sample. Conventional blowback methods are typically unable to prevent sample lines from clogging by sticky, reactive gases and condensation of chemical reactions. In fact, in certain instances, conventional blowback appears to make clogging matters worse as it tends to quickly cool down a respective sample line and filter, resulting in subsequent condensation or the reformation of contaminants such as NH$_4$Cl on inner walls of the sample line being cleaned.

Embodiments herein can include operating in a so-called flow back or back flush mode. The flow back mode (FIG. 2) can be operated before and/or after operating in the sampling mode as discussed in FIG. 1.

Figure 2:
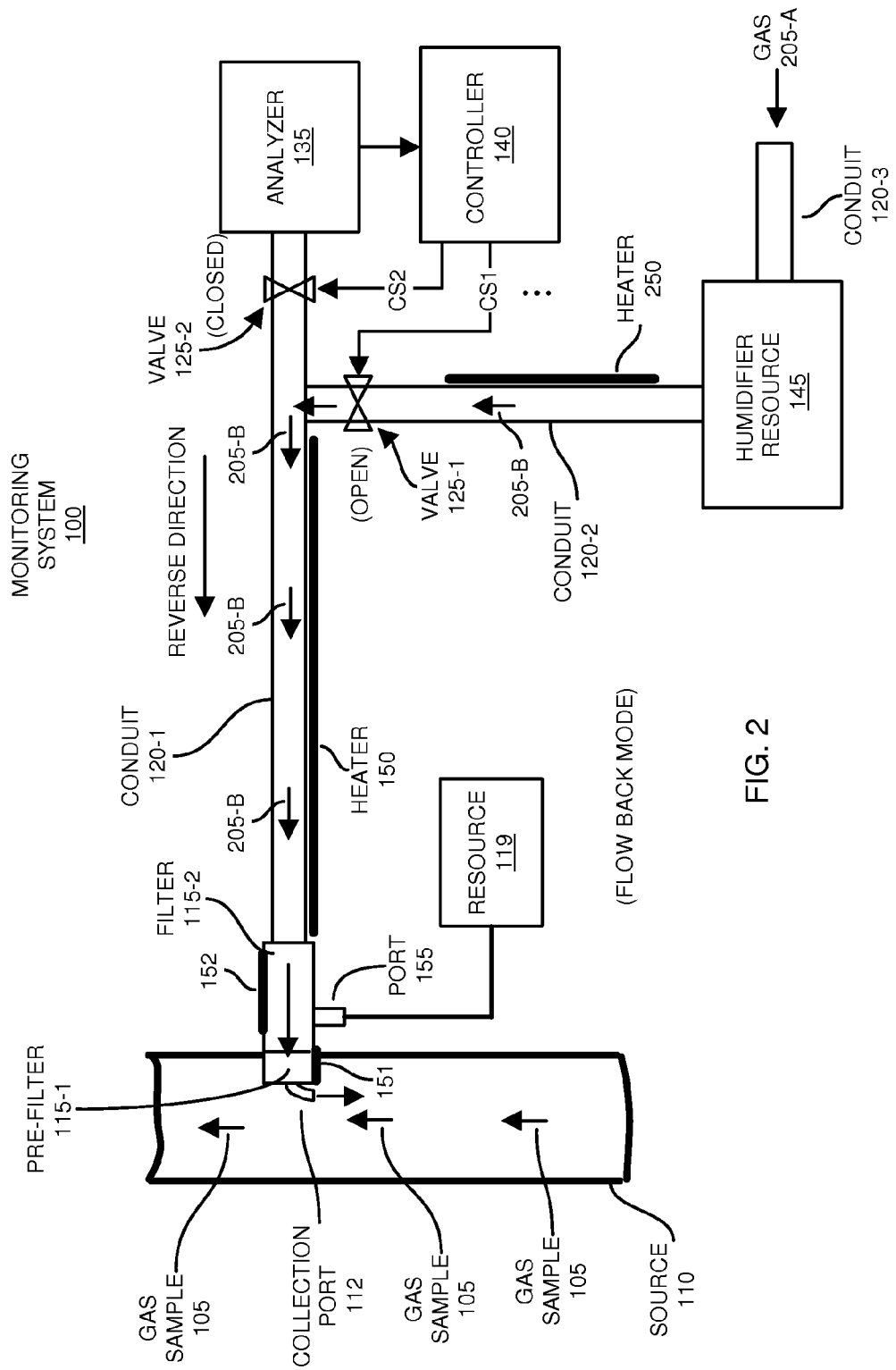
FIG. 2 is an example diagram illustrating a monitoring system operating in a flow back mode according to embodiments herein.
Figure 3:
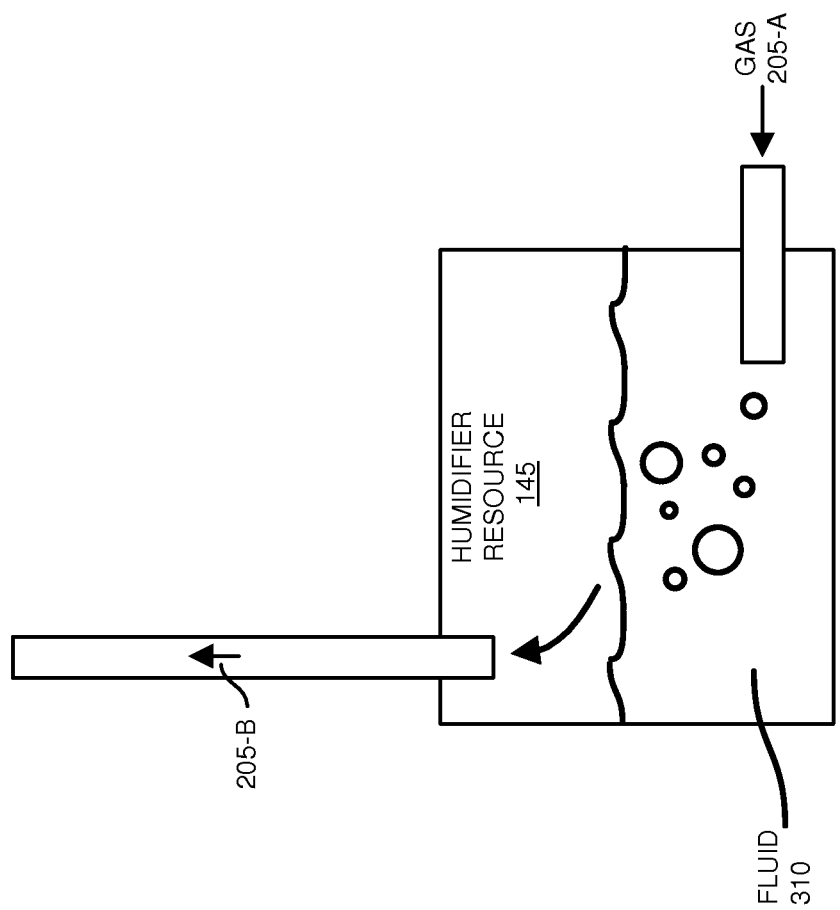
FIG. 3 is an example diagram illustrating generation of a humidified gas according to embodiments herein.
Figure 4:
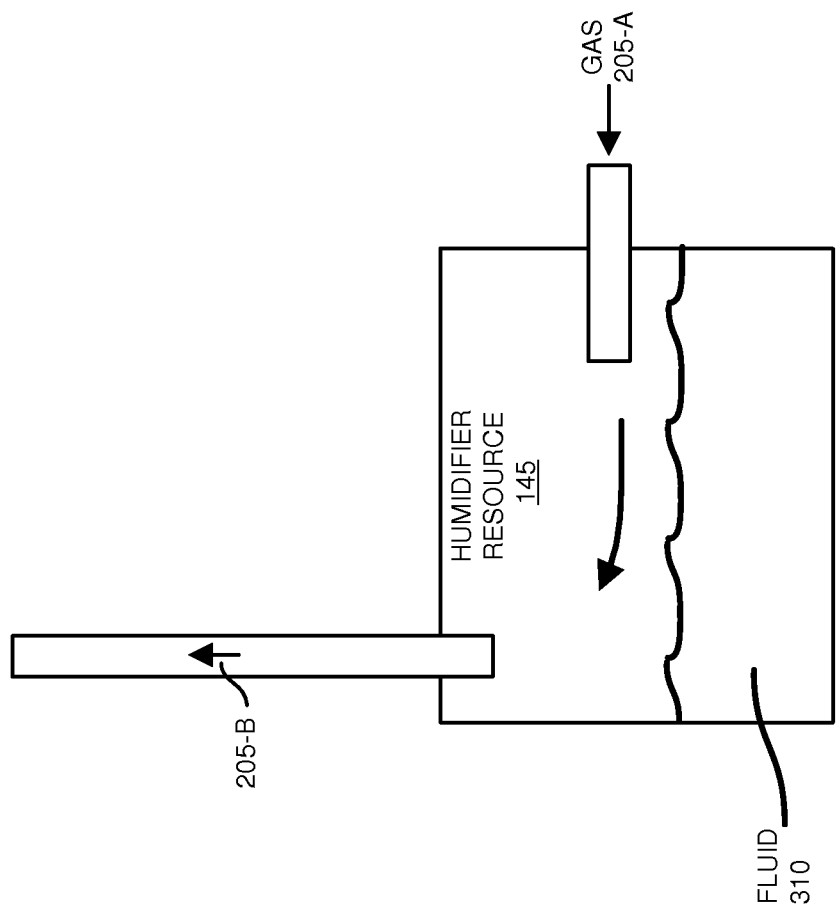
FIG. 4 is an example diagram illustrating generation of a humidified gas according to embodiments herein.

More specifically, FIG. 2 is an example diagram illustrating a technique of reducing buildup of contaminants in a sample line according to embodiments herein. Note that FIG. 3 and FIG. 4 are only two examples of humidifiers. Any suitable resource or type of humidifier control device (e.g., heated humidifier, ultrasonic humidifier, peltier for heat control, etc.) can be used to produce humidified gas.

As shown in FIG. 2, when operating in a so-called flow back mode, via generation of control signal CS2, the controller 140 controls the valve 125-2 at the end of the conduit 120-1 opposite the source 110 to be in a CLOSED position. The closed position of valve 125-2 prevents a flow of the gas sample 105 from the source 110 to the gas analyzer 135. Further, in the flow back mode, via generation of control signal CS1, the controller 140 controls the valve 125-1 to an OPEN position to facilitate passing of humidified gas 205-B from the humidifier resource 145 though the conduit 120-2 and conduit 120-1 in a reverse direction towards the source 110.

Humidifier resource 145 receives gas 205-A through conduit 120-3 and produces humidified gas 205-B, which passes though conduit 120-2 to conduit 120-1 in the flow back mode.

In contrast to conventional blowback techniques, in general, embodiments herein include novel techniques of reducing a degree to which contaminants in gas sample 105 are able to adhere to inner walls of a sample line. For example, in the flow back mode according to embodiments herein, the controller 140 controls valves 125 to input humidified gas 205-B through at least a portion of conduit 120-1 towards source 110. As its name suggests, the humidified gas 205-B includes some amount of water. Exposing the inner surfaces of conduit 120-1 to the humidified gas 205-B to a gas including water causes one or more layers of water to be adsorbed onto the inner surfaces of conduit 120-1.

The adsorption of the one or more layers of water (or other suitable substance) of water (or other contaminant solvent) on the inner surface of conduit 120-1 can serve one or more purposes.

For example, inputting the humidified gas 205-B in the reverse direction through at least a portion of the conduit 120-1 can prevent or reduce an amount of water soluble substances such as Ammonia (e.g., NH3), Hydrochloric Acid (e.g., HCl), Ammonium Chloride (e.g., NH4Cl), Ammonium Nitrate (NH4NO3) Ammonium Sulfate (e.g., (NH4)2SO4), etc., in the sample gas 105 from subsequently adhering to the inner surface of the conduit 120-1 when sampling again. For example, the one or more layers of water (or other solvent) inhibits the contaminants in the gas sample 105 from sticking to the inner walls of conduit 120-1 and/or filters 115.

In addition to preventing at least a portion of the contaminants in the gas sample 105 from sticking to the inner surface of the conduit 120-1, the passing of the humidified gas 205-B through the conduit 120-1 can serve to clean or remove one or more contaminants such as Ammonia (e.g., $NH_3$), Hydrochloric Acid (e.g., HCl), Ammonium Chloride (e.g., $NH_4Cl$), Ammonium Nitrate (NH4NO3), Ammonium Sulfate (e.g., $(NH_4)_2SO_4$), etc., from the inner surface of the conduit 120-1.

Thus, even though the inner surface of the conduit 120-1 may be coated with water or other suitable substance during a flow back mode, assuming that the gas sample 105 from the source includes contaminants, at least a portion of contaminants in the gas sample may adhere to an inner surface of the conduit 120-1. Passing the humidified gas 205-B through the conduit 120-1 may also have the affect of removal of contaminants on the inner surface of conduit 120-1 and filters 115.

In accordance with one embodiment, the monitoring system 100 at least occasionally switches between operating in the sampling mode and the flow back mode to reduce buildup of contaminants in the gas sample 105 on an inner surface of the conduit 120-1 and filter 115 (e.g., pre-filter 115-1 and filter 115-2).

As previously discussed, one embodiment herein includes adsorbing one or more layers of water (or other suitable solvent) onto the inner surface of the conduit 120-1 and filters 115. To support adsorption, as opposed to condensation on the inner surface of conduit 120-1, the concentration of water in the humidified gas 205-B can be maintained at an appropriate level such that the water in the humidified gas 205-B does not condense onto the inner surface of the conduit 120-1 during the flow back mode. By way of a non-limiting example, the relative humidity of the humidified gas 205-B as it passes through the conduit 120-1 may fall between a range between 25% and 95% to prevent condensing.

The setting of the relative humidity and/or concentration of water in the humidified gas 205-B can affect how much water is adsorbed onto the inner surface of the conduit 120-1. For example, a higher concentration of water in the humidified gas 205-B can result in more water being adsorbed onto the inner surface of the conduit 120-1; a lower concentration of water in the humidified gas 205-B can result in less water being adsorbed onto the inner surface of the conduit 120-1. The desired amount of water to adsorb onto the inner walls can vary depending on the embodiment. In certain instances, it may be desirable to dynamically adjust the concentration of water in the humidified gas 205-B depending on a respective concentration of contaminants in the gas sample 105.

Condensation of water on the inner surface conduit 120-1 may be undesirable in certain instances because the subsequent evaporation of water from any condensed water (during a subsequent forward flow sampling mode) on an inner surface of the conduit can interfere with subsequent testing of contaminants in the gas sample by the gas analyzer. That is, if water condenses on the inner surface of the conduit 120-1 when passing the humidified gas 205-B through the confidence 120-1, subsequent evaporation of the water off of the inner surface during the sampling mode may impede the ability of the gas analyzer to accurately determine an actual concentration of contaminants present in the gas sample 105.

In one embodiment, the monitoring system 100 includes heater 250 to heat the humidified gas 205-B to the appropriate temperature. In one embodiment, the heater 250 heats the humidified gas 205-B in the conduit 120-2 to a temperature of around 185 degree Celsius although this temperature may vary depending on the embodiment.

In one embodiment, the controller 140 controls a volume of the flow of humidified gas 205-B through conduit 120-2 and conduit 120-1 to fall within a range between one and twenty liters per minute although the flow rate may vary depending on the embodiment. However, depending on the embodiment, the volume can be any suitable outside of this range as well.

FIG. 3 is an example diagram illustrating generation of humidified gas according to embodiments herein.

As shown in FIG. 3, the humidifier resource 145 can be configured to receive gas 205-A (e.g., zero air, ambient air, etc.) from any suitable source. The gas 205-A can be filtered to remove contaminant and or particulate matter.

By way of a non-limiting example, to generate the humidified gas 205-B, the humidifier resource 145 bubbles the received gas 205-A through a reservoir of fluid 310. The fluid 310 can be any suitable type of fluid such as de-ionized water, distilled water, purified water, etc.

By way of a non-limiting example, when the fluid 310 is a solvent such as water, exposing the received gas 205-A to the fluid 310 increases a concentration of the amount of water in the gas 205-A to a desired level to produce humidified gas 205-B, which is used to adsorb one or more layers of water onto the inner surface. The concentration of the water in the humidified gas 205-B can be controlled to prevent condensation of water on the inner surface of the conduit 120-1 when the humidified gas 205-B is passed through the conduit in the flow back mode.

The contaminants such as HCl, $NH_3$, $NH_4Cl$, etc., are all water soluble. As mentioned, the flow back of hot and/or humidified (wet) zero air (e.g., humidified gas 205-B) into the conduit 120-1 facilitates removal of these compounds from wall surfaces of the conduit 120-1. Heating of the humidified gas 185 to be above a threshold value such as 150 degrees Celsius, speeds up removal of the soluble HCl, $NH_3$, $NH_4Cl$, etc., on the inner surface of the conduit 120-1 and filters 115.

FIG. 4 is an example diagram illustrating generation of a humidified gas according to embodiments herein.

As shown in FIG. 4, the humidifier resource 145 receives gas 205-A (e.g., zero air, ambient air, etc.) from any suitable source. To generate the humidified gas 205-B, the humidifier resource 145 passes the received gas 205-A over a reservoir of fluid 310. As mentioned, the fluid 310 can be any suitable type of fluid such as de-ionized water, distilled water, purified water, etc.

By further way of a non-limiting example, when the fluid 310 is water, exposing the received gas 205-A to the fluid 310 increases a concentration of the amount of water in the gas 205-A to a desired level to produce humidified gas 205-B.

As previously discussed, the concentration of the water in the humidified gas 205-B can be controlled to prevent condensation of water on the inner surface of the conduit 120-1 when the humidified gas 205-B is passed through the conduit in the flow back mode.

Figure 5:
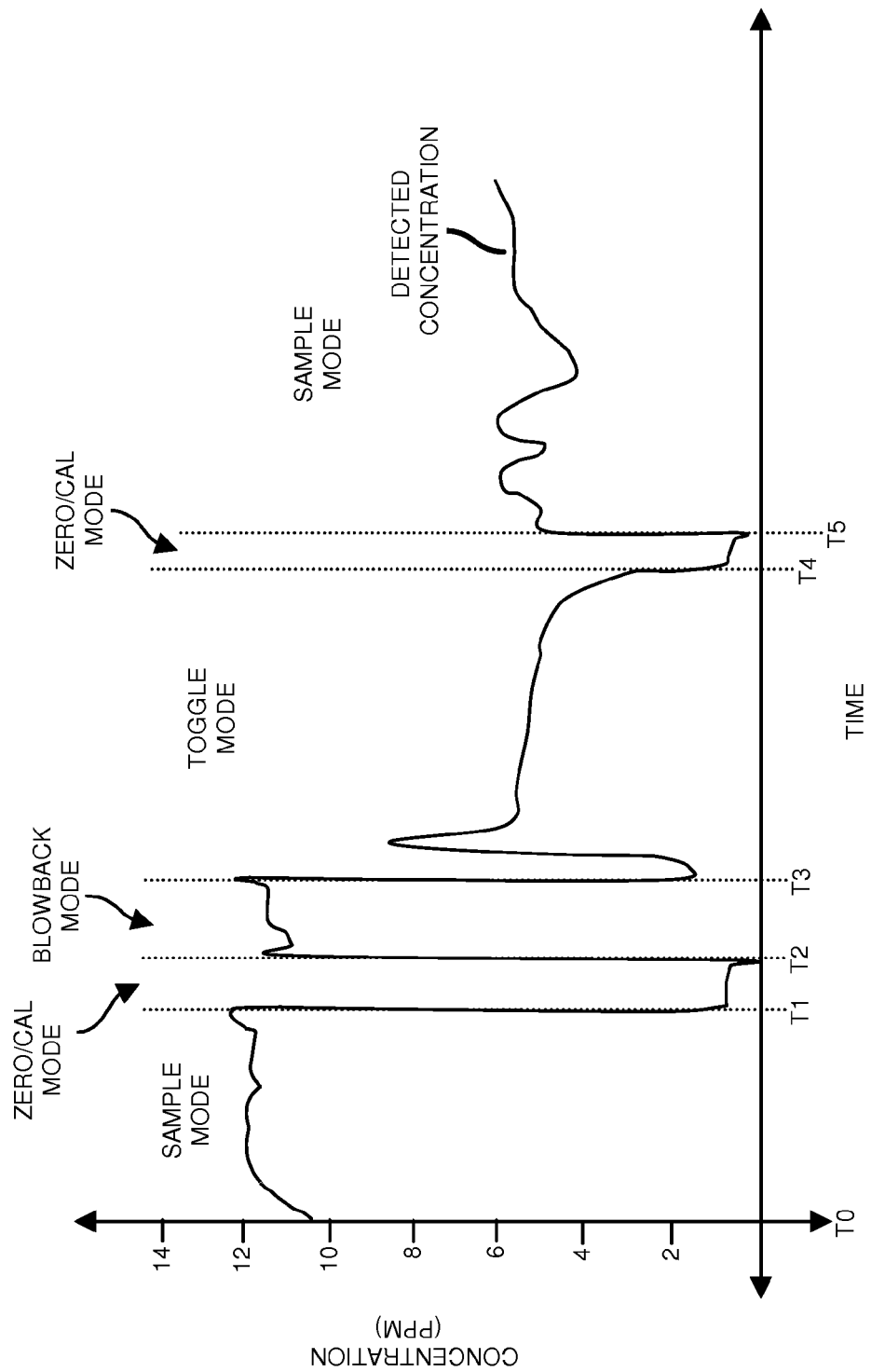
FIG. 5 is an example timing diagram illustrating operation of the monitoring system in different modes according to embodiments herein.

FIG. 5 is an example timing diagram illustrating operation of the monitoring system in different modes according to embodiments herein.

As shown, the monitoring system 100 can be operated in multiple different modes. By way of a non-limiting example, the time on the time axis between T0 and T4 can represent 9 hours of linear time.

In this example embodiment, between time T0 and T1, the controller 140 controls monitoring system 100 to operate in a sampling mode as previously discussed with respect to FIG. 1. In the sampling mode, the analyzer 135 continuously or repeatedly monitors concentrations of one or more contaminants in the received gas sample 105 without switching over to another mode.

One or more resources in the monitoring system 105 may need occasional calibration or cleaning. In this example embodiment, between time T1 and T2, the controller 140 controls monitoring system 100 to operate in a zero mode and/or calibration mode. In the zero/cal mode, valve 125-2 is OPEN, valve 125-1 is CLOSED.

Operating in the zero mode can include receiving a zero gas (e.g., ambient air, purified air, etc.) from resource 119 and inputting the received gas into port 155 to clean filter 115 and/or other parts of monitoring system 100. In accordance with one example embodiment, when inputting the gas into port 155, a first portion of the gas received on port 155 flows through pre-filter 115-1 and out of collection port 112 into source 110. Another portion of the zero gas received on port 155 flows though filter 115-2 and conduit 120-1 to analyzer 135. In one embodiment, the controller 140 controls a flow of the zero and/or calibration gas into port 155.

If desired, during the zero/cal mode, a calibration sample having a known level of one or more contaminants can be inputted into port 155. In one example embodiment, conduit 120-1 conveys at least a portion of the calibration sample to analyzer 135 for calibration of analyzer 135.

Between time T2 and T3, the monitoring system 100 can be operated in a so-called blowback mode in which bursts of a gas are inputted to port 155 to clean collection port 112, pre-filter 115-1, and/or filter 115-2 of undesirable contaminants and/or particulate matter.

Between time T3 and time T4, the monitoring system 100 operates in a so-called toggle mode in which the controller 140 repeatedly switches between operating the monitoring system 100 in the sample mode (FIG. 1) and the flow back mode (FIG. 2). More details of operating the monitoring system 100 in the toggle mode are shown and discussed in FIG. 6.

Between time T4 and T5, the monitoring system 100 operates in a zero mode and/or calibration mode.

Subsequent to time T5, the monitoring system 100 operates in the sample mode again.

Note further that the ordering of operating the different modes in FIG. 5 is shown by way of non-limiting example only and that the controller 140 can initiate any suitable order of monitoring the modes. For example, as discussed below, the controller 140 can operate the monitoring system 100 in the sample mode and selectively switch to operating in the toggle mode in response to detecting a trigger condition.

Figure 6:
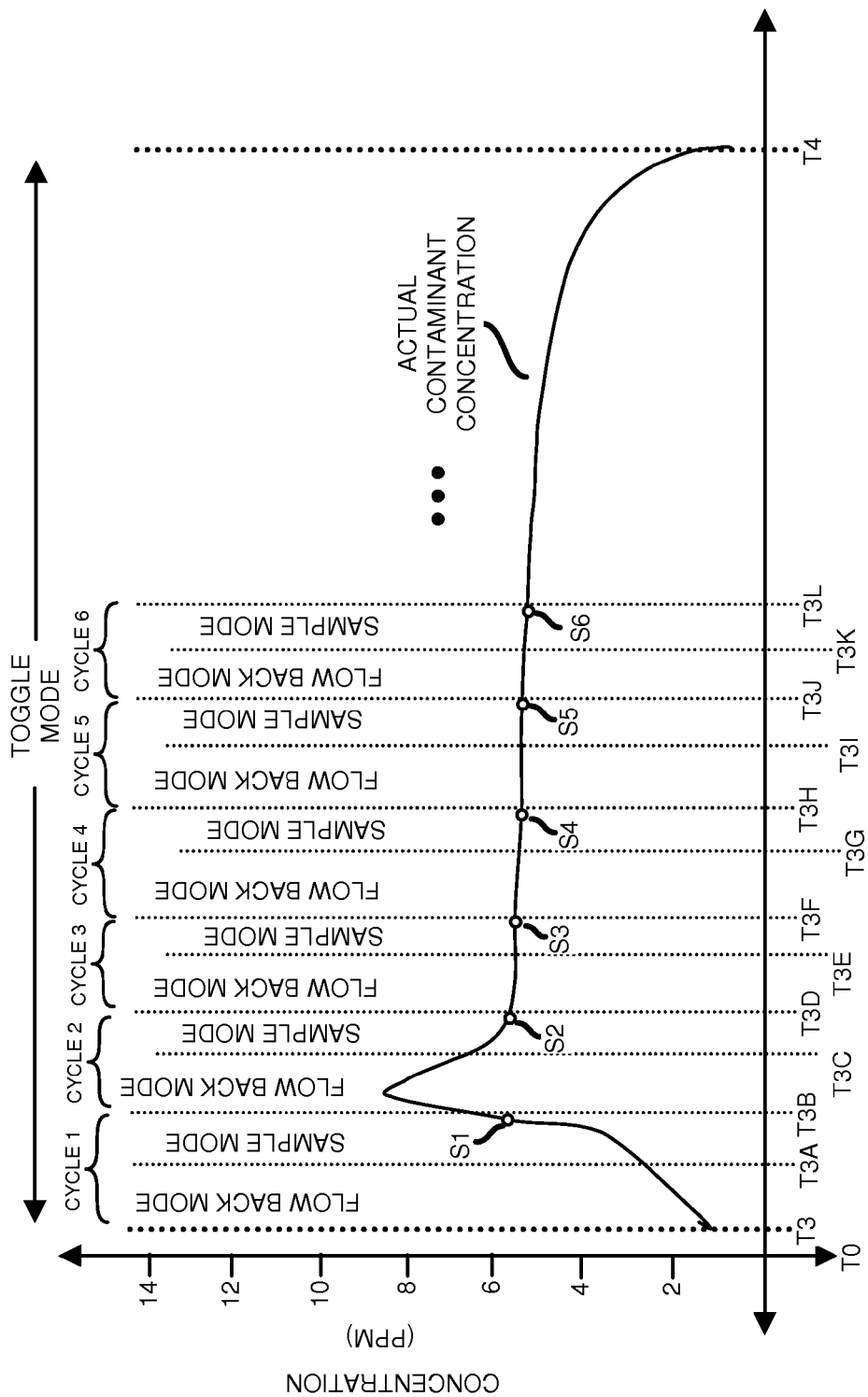
FIG. 6 is an example timing diagram illustrating operation of the monitoring system in different modes according to embodiments herein.

FIG. 6 is an example timing diagram illustrating operation of the monitoring system in the toggle mode according to embodiments herein.

As previously discussed, one embodiment herein includes operating the monitoring system 100 as a continuous emissions monitoring system. In one embodiment, system 100 and corresponding methods as discussed herein continuously monitors emission from the smokestack.

In order prevent downtime caused by contaminants clogging or impairing use of the conduit 120-1 and/or other resources such as pre-filter 115-1, filter 115-2, etc., embodiments herein include operating monitoring system 100 to cycle between the flow back mode and sample mode at a desired rate as shown. In one embodiment, the contaminants in the received gas sample do not necessarily cause line clogging. Mere presence of contaminants on the conduit walls can adversely impact sample measurements during the sample mode. Embodiments herein include preventing such contaminants from adhering to the inner conduit walls.

In accordance with such an embodiment of operating in the toggle mode, the monitoring system 100 can be operated in the flow back mode (FIG. 2) in a first portion of a respective cycle; the monitoring system 100 can be operated in the sample mode (FIG. 1) in a second portion of a respective cycle. Operating in this cyclical manner reduces an amount of contaminants that adhere to the conduit, yet it provides repeated measurements of the contaminants in gas sample 105 over time.

Assume in this example that the monitoring system 100 operates in a 15 minute running cycle. In this example embodiment, the monitoring system 100 operates in a flow back mode for a first portion of time such as 9 minutes. No samples are taken during the first portion of time of the cycle. The monitoring system 100 is then switched to the sample mode for a second portion of time such as 6 minutes. After sufficient flushing of the conduit 120-1 with gas sample 105 during the second portion of time, such as during a last minute (or few minutes) of a cycle, the analyzer 135 performs one or more sample measurements of the one or more contaminants in the gas sample 105. In this example embodiment, there would be one or more measurements for each cycle of time.

More specifically, in the toggle mode, the time between T3 and time T3B in FIG. 6 represents a first cycle; the time between T3B and time T3D represents a second cycle; the time between T3D and time T3F represents a third cycle; the time between T3F and time T3H represents a fourth cycle; the time between T3H and time T3J represents a fifth cycle; the time between T3J and time T3L represents a sixth cycle; and so on.

In a first portion (e.g., between T3 and T3B) of the first cycle (i.e., cycle 1), the monitoring system 100 operates in the flow back mode as previously discussed with respect to FIG. 2. In a second portion (e.g., between T3A and T3B) of the first cycle, the monitoring system 100 operates in the sampling mode as previously discussed in FIG. 1. In one embodiment, as mentioned, to ensure an accurate measurement, the analyzer 135 measures a level of one or more contaminants (shown as sampling S1) in the gas sample 105 after operating in the sample mode for sufficient amount of time that the gas sample 105 appropriately floods the conduit 120-1 and reaches analyzer 135.

In a first portion (e.g., between T3B and T3C) of the second cycle (i.e., cycle 2), the monitoring system 100 operates in the flow back mode as previously discussed with respect to FIG. 2. In a second portion (e.g., between T3C and T3D) of the second cycle, the monitoring system 100 operates in the sampling mode as previously discussed in FIG. 1. In one embodiment, to ensure an accurate measurement, the analyzer 135 measures a level of one or more contaminants (shown as sampling S2) in the gas sample 105 after operating in the sample mode for sufficient amount of time that the gas sample 105 appropriately floods the conduit 120-1 and reaches analyzer 135.

In a first portion (e.g., between T3D and T3E) of the third cycle (i.e., cycle 3), the monitoring system 100 operates in the flow back mode as previously discussed with respect to FIG. 2. In a second portion (e.g., between T3E and T3F) of the third cycle, the monitoring system 100 operates in the sampling mode as previously discussed in FIG. 1. In one embodiment, to ensure an accurate measurement, the analyzer 135 measures a level of one or more contaminants (shown as sampling S3) in the gas sample 105 after operating in the sample mode for sufficient amount of time that the gas sample 105 appropriately floods the conduit 120-1 and reaches analyzer 135 again.

In a first portion (e.g., between T3F and T3G) of the fourth cycle (i.e., cycle 4), the monitoring system 100 operates in the flow back mode as previously discussed with respect to FIG. 2. In a second portion (e.g., between T3G and T3H) of the fourth cycle, the monitoring system 100 operates in the sampling mode as previously discussed in FIG. 1. In one embodiment, to ensure an accurate measurement, the analyzer 135 measures a level of one or more contaminants (shown as sampling S4) in the gas sample 105 after operating in the sample mode for sufficient amount of time that the gas sample 105 appropriately floods the conduit 120-1 and reaches analyzer 135 again.

In a first portion (e.g., between T3H and T3I) of the fifth cycle (i.e., cycle 5), the monitoring system 100 operates in the flow back mode as previously discussed with respect to FIG. 2. In a second portion (e.g., between T3I and T3J) of the fifth cycle, the monitoring system 100 operates in the sampling mode as previously discussed in FIG. 1. In one embodiment, to ensure an accurate measurement, the analyzer 135 measures a level of one or more contaminants (shown as sampling S5) in the gas sample 105 after operating in the sample mode for sufficient amount of time that the gas sample 105 appropriately floods the conduit 120-1 and reaches analyzer 135 again.

In a first portion (e.g., between T3J and T3K) of the sixth cycle (i.e., cycle 6), the monitoring system 100 operates in the flow back mode as previously discussed with respect to FIG. 2. In a second portion (e.g., between T3K and T3L) of the sixth cycle, the monitoring system 100 operates in the sampling mode as previously discussed in FIG. 1. In one embodiment, to ensure an accurate measurement, the analyzer 135 measures a level of one or more contaminants (shown as sampling S6) in the gas sample 105 after operating in the sample mode for sufficient amount of time that the gas sample 105 appropriately floods the conduit 120-1 and reaches analyzer 135 again.

Accordingly, during the toggle mode, in the toggle mode, the monitoring system 100 switches between operating in the flow back mode and the sample mode.

Note that the monitoring system 100 can initiate the toggle mode (e.g., switching between the flow back mode and the sample mode) depending detected settings on one or more monitored parameters.

As an example, while in any mode, the controller 140 can be configured to monitor the different concentrations of contaminants. Embodiments herein can include (the controller 140) detecting that a concentration of one or more contaminants in the gas sample 105 is above a threshold value. In such an instance, when the concentration of contaminants in the gas sample 105 is a high level, it is more likely that contaminants will adhere to the inner surface of the conduit 120-1.

In one embodiment, in response to detecting that a concentration of contaminants in the gas sample 105 is above a threshold value, the controller 140 can initiate setting the monitoring system 100 to the toggle mode (FIG. 6) in which the monitoring system 100 is toggled between operating in the flow back mode (FIG. 2) and the sample mode (FIG. 1) to prevent or reduce buildup of contaminants from the gas sample onto an inner surface of the conduit 120-1.

In one embodiment, the monitoring system 100 can be configured to detect a concentration of Ammonia in the gas sample 105. If the concentration of detected Ammonia in the gas sample 105 is above a threshold value such as 11 parts per million, the monitoring system 100 can be set to operate in the toggle mode.

If the concentration of contaminants is below a threshold value such as 8 parts per million, the monitoring system 100 need not operate in the toggle mode and can switch out of the toggle mode to a continuous sampling mode as previously discussed. However, at least occasionally, while in the continuous sample mode, it may be desirable to operate in the flow back mode to clean the inner surface of the conduit and/or adhere one or more layers of water to the inner surface.

Note that the trigger condition to switch to the toggle mode can be based at least in part on time as well. For example, while operating in the continuous sample mode, in response to detecting that a concentration of contaminants in the gas sample 105 is above a threshold concentration value for more than a threshold amount of time, the monitoring system 100 can be configured to switch to the toggle mode as shown in FIG. 6.

In accordance with yet further embodiments, note that the duration of the cycles in the toggle mode and duration of the flow back mode versus the sample mode in a respective cycle can vary over time. For example, if the concentration of a contaminant of interest in the gas sample 105 is relatively low such that little or none of the contaminant would adhere to the inner surface of conduit 120-1, the duration of the cycle itself and/or duration of the flow back mode (versus sample mode in a cycle) can be lengthened because there is less urgency to operate in the flow back mode.

In accordance with yet further embodiments, the controller 140 can initiate switching from operating in the toggle mode to operating in the sample mode in response to detecting that the concentration of contaminants in the gas sample 105 falls below a threshold value.

Additionally, there may be circumstances in which it is desirable to operate in the sample mode to obtain a higher number of contaminant measurements within a duration of time. In such an instance, the controller 140 can initiate operating in the sample mode.

Figure 7:
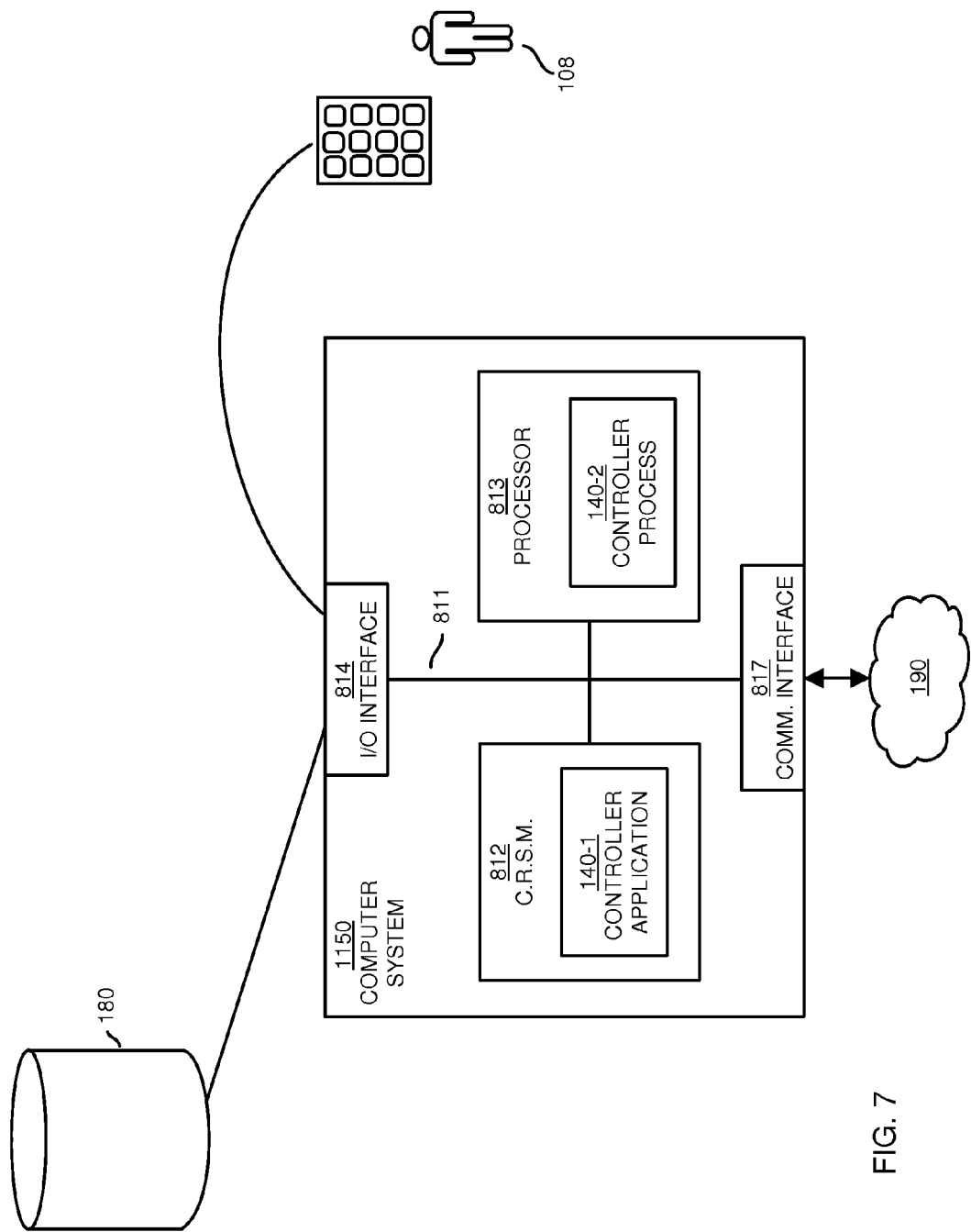
FIG. 7 is a diagram illustrating an example architecture on which to execute methods according to embodiments herein.

FIG. 7 is an example block diagram of a computer system 1150 for implementing any of the control operations according to embodiments herein. In one embodiment, the controller 140 includes computer system 1150 that carries out control operations based on execution of software instructions, logic, etc.

As shown, computer system 1150 of the present example can include an interconnect 811 that couples computer readable storage media 812 such as a non-transitory type of media (i.e., any type of hardware storage medium) in which digital information can be stored and retrieved, a processor 813 (e.g., one or more processor devices), I/O interface 814, and a communications interface 817.

I/O interface 814 provides connectivity to a repository 180 and, if present, other devices such as display screen, keypad, a computer mouse, etc.

Computer readable storage medium 812 can be any non-transitory storage device such as memory, optical storage, hard drive, floppy disk, etc. In one embodiment, the computer readable storage medium 812 stores instructions and/or data.

Communications interface 817 enables the computer system 1150 and processor 813 to communicate over a resource such as network 190 to retrieve information from remote sources and communicate with other computers. Depending on the embodiment, any or all of the functionality associated with the controller application 140-1 can be performed locally by processor 813, or via resources in network 190, or a combination of both. Controller application 140 controls operation of the monitoring system 100 in the different modes.

I/O interface 814 enables processor 813 to retrieve or attempt retrieval of stored information from repository 180.

As shown, computer readable storage media 812 is encoded with controller application 140-1 (e.g., software, firmware, etc.) executed by processor 813. Controller application 140-1 can be configured to include instructions to implement any of the operations associated with controller 140 as previously discussed.

During operation of one embodiment, processor 813 accesses computer readable storage media 812 via the use of interconnect 811 in order to launch, run, execute, interpret or otherwise perform the instructions in controller application 140-1 stored on computer readable storage medium 812.

Execution of the controller application 140-1 produces processing functionality such as controller process 140-2 in processor 813. In other words, the controller process 140-2 associated with processor 813 represents one or more aspects of executing controller application 140-1 within or upon the processor 813 in the computer system 1150.

Those skilled in the art will understand that the computer system 1150 can include other processes and/or software and hardware components, such as an operating system that controls allocation and use of hardware resources to execute controller application 140-1.

In accordance with different embodiments, note that computer system may be any of various types of devices, including, but not limited to, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. The computer system 1150 and/or functionality supported by the controller application 140 may reside or be moved to any location.

Functionality supported by the monitoring system 100 as controlled by controller application 140 will now be discussed via the flowchart in FIG. 8. Note that the processing blocks in the flowchart below can be executed in any suitable order and further summarize the embodiments as discussed herein.

Figure 8:
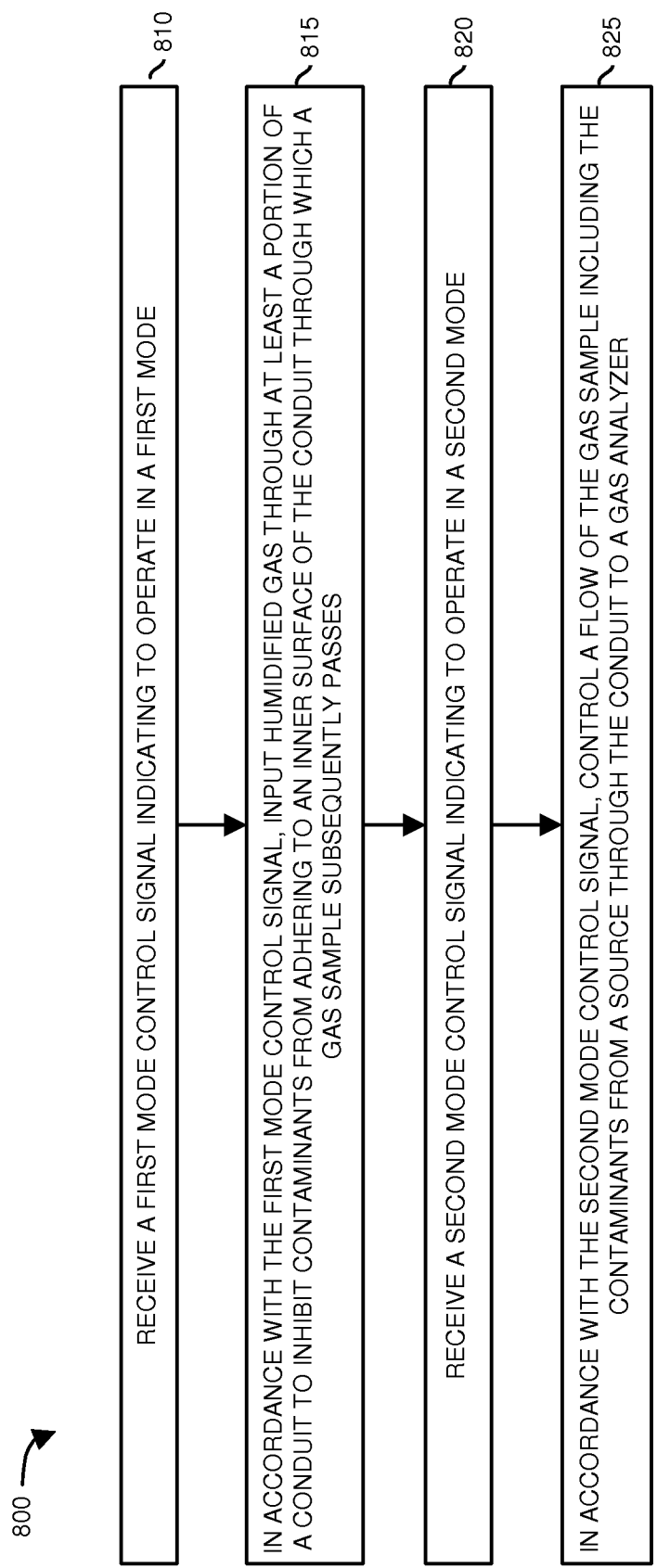
FIG. 8 is flowchart illustrating an example method according to embodiments herein.

FIG. 8 is a flowchart 800 illustrating an example method according to embodiments herein. Note that there will be some overlap with respect to concepts as discussed above.

In processing block 810, the monitoring system 100 receives a first mode control signal indicating to operate in a first mode.

In processing block 815, in accordance with the first mode control signal, the controller 140 inputs humidified gas through at least a portion of the conduit 120-1 to inhibit contaminants from adhering to an inner surface of the conduit 120-1 through which a gas sample 105 subsequently passes.

In processing block 820, the monitoring system 100 receives a second mode control signal indicating to operate in a second mode.

In processing block 825, in accordance with the second mode control signal, the controller 140 controls a flow of the gas sample 105 including the contaminants from a source 110 (such as an emission source) through the conduit 120-1 to analyzer 135.

Note again that techniques herein are well suited for use in contaminant monitoring systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
   receiving a first mode control signal indicating to operate in a first mode;
   in accordance with the first mode control signal, inputting humidified gas through at least a portion of a conduit to adsorb a layer of water onto an inner surface of the conduit;
   receiving a second mode control signal indicating to operate in a second mode;
   in accordance with the second mode control signal, controlling a flow of a gas sample including water soluble contaminants from a source through the conduit to a gas analyzer, wherein the layer of water inhibits the water soluble contaminants from adhering to the inner surface of the conduit; and
   in response to detecting that a concentration of a particular water soluble contaminant in the gas sample is above a threshold value, toggling between operating in the first mode and the second mode to reduce buildup of the particular water soluble contaminant on the inner surface of the conduit.

2. The method as in claim 1, wherein the source is a smokestack, the method further comprising:
   performing continuous emissions monitoring of the smokestack.

3. The method as in claim 1, wherein inputting the humidified gas through at least the portion of the conduit includes inputting the humidified gas in a first direction through the conduit; and
   wherein controlling the flow of the gas sample including the water soluble contaminants from the source through the conduit to the gas analyzer includes controlling the flow of the gas in a second direction through the conduit, the second direction being substantially opposite the first direction.

4. The method as in claim 1, wherein controlling the flow of the gas sample causes at least a portion of the water soluble contaminants in the gas sample to adhere to the inner surface of the conduit; and
   toggling to the first mode removes the portion of the water soluble contaminants from the inner surface of the conduit via input of the humidified gas.

5. The method as in claim 4 further comprising:
   controlling the gas analyzer to sample presence of water soluble contaminants in the gas sample while in the second mode.

6. The method as in claim 1 further comprising:
   heating at least a portion the conduit to a temperature above a boiling point of the gas sample; and
   controlling the humidified gas to include a concentration of water between 0.1% and 95.0%.

7. The method as in claim 1 further comprising:
   controlling a concentration of water in the humidified gas to be within a range that prevents condensation of the water on the inner surface of the conduit during the first mode.

8. The method as in claim 1 wherein:
   the concentration of the particular water soluble contaminant in the gas sample is above the threshold concentration value for more than a threshold amount of time.

9. The method as in claim 1 further comprising:
   in response to receiving the first mode control signal:
     controlling a first valve at the end of the conduit opposite the source to be in a closed position, the closed position of the first valve preventing a flow of the gas sample from the source to the gas analyzer; and
     controlling a second valve to an open position to facilitate passing of the humidified gas from the humidifier resource though the conduit in the reverse direction to the source.

10. The method as in claim 9 further comprising:
    in response to receiving the second mode control signal:
      controlling the first valve to be in an open position, the open position of the first valve causing a flow of the gas sample from the source to the gas analyzer; and
      controlling the second valve to a closed position to prevent the humidified gas from being inputted into the conduit.

11. The method as in claim 1 further comprising:
    heating the humidified gas prior to inputting the humidified gas through the conduit.

12. The method as in claim 1 wherein:
    toggling between the first mode and second mode to provides a substantially continuous flow of gases through the conduit either in the forward direction or reverse direction.

13. The method as in claim 1, wherein inputting the humidified gas through at least a portion of the conduit includes causing the humidified gas to flow in a first direction through the conduit, and
    wherein controlling the flow of the gas sample includes causing the gas sample including the water soluble contaminants to flow in a second direction through the conduit, the second direction opposite the first direction.

14. A system comprising:
    a conduit; and
    a controller, the controller configured to:
      in a first mode, input humidified gas through at least a portion of the conduit to adsorb a layer of water onto an inner surface of the conduit, and
      in a second mode, control a flow of a gas sample including water soluble contaminants from a source through the conduit to a gas analyzer, wherein the layer of water inhibits the water soluble contaminants from adhering to the inner surface of the conduit
wherein the controller toggles between operating in the first mode and the second mode to reduce buildup of a particular water soluble contaminant on the inner surface of the conduit in response to detecting that a concentration of the particular water soluble contaminant in the gas sample is above a threshold value.

15. The system as in claim 14, wherein the humidified gas passes through the conduit in a first direction; and
wherein the gas sample passes through the conduit in a second direction, the second direction being opposite the first direction.

16. The system as in claim 14, where the source is a smokestack, the system monitoring continuously monitoring emissions from the smokestack.

17. The system as in claim 14, wherein the controller toggles to the first mode to remove the particular water soluble contaminant from the inner surface of the conduit via input of the humidified gas.

18. The system as in claim 14 further comprising:
a humidifier resource that produces the humidified gas to include a concentration of water between 0.1% and 95.0%.

19. The system as in claim 14 further comprising:
a humidifier resource configured to control a concentration of water in the humidified gas to be within a range that prevents condensation of the water on the inner surface of the conduit during the first mode.

20. The system as in claim 14 further comprising:
a first valve;
a second valve; and
in the first mode, the controller configured to:
control the first valve to be in a closed position, the closed position of the first valve preventing a flow of the gas sample from the source to the gas analyzer; and
control the second valve to an open position to facilitate passing of the humidified gas from the humidifier resource though the conduit in the reverse direction to the source.

21. The system as in claim 20 further comprising:
in the second mode, the controller configured to:
control the first valve to be in an open position, the open position of the first valve causing a flow of the gas sample from the source to the gas analyzer; and
control the second valve to a closed position to prevent the humidified gas from being inputted into the conduit.

22. A system comprising:
at least one processor device; and
a hardware storage resource coupled to the at least one processor device, the hardware storage resource storing instructions that, when executed by the at least one processor device, cause the at least one processor device to perform the operations of:
in accordance with a first mode of a monitoring system, inputting humidified gas through at least a portion of a conduit to adsorb a layer of water onto an inner surface of the conduit;
in accordance with a second mode of a monitoring system, controlling a flow of the gas sample including the water soluble contaminants from a source through the conduit to a gas analyzer, wherein the layer of water inhibits the water soluble contaminants from adhering to the inner surface of the conduit; and
in response to detecting that a concentration of a particular water soluble contaminant in the gas sample is above a threshold value, toggling between operating in the first mode and the second mode to reduce buildup of the particular water soluble contaminant on the inner surface of the conduit.

23. Computer-readable storage hardware having instructions stored thereon, the instructions, when carried out by at least one processing device, causes the at least one processing device to perform operations of:
in accordance with a first mode of a monitoring system, inputting humidified gas through at least a portion of a conduit to adsorb one or more layers of water onto an inner surface of the conduit;
in accordance with a second mode of a monitoring system, controlling a flow of the gas sample including the water soluble contaminants from a source through the conduit to a gas analyzer, wherein the layer of water inhibits the water soluble contaminants from adhering to the inner surface of the conduit; and
in response to detecting that a concentration of a particular water soluble contaminant in the gas sample is above a threshold value, toggling between operating in the first mode and the second mode to reduce buildup of the particular water soluble contaminant on the inner surface of the conduit.

* * * * *